(12) United States Patent
Dolan et al.

(10) Patent No.: US 9,486,340 B2
(45) Date of Patent: Nov. 8, 2016

(54) METHOD FOR MANUFACTURING A STENT AND STENT MANUFACTURED THEREBY

(71) Applicant: Medtronic Vascular, Inc., Santa Rosa, CA (US)

(72) Inventors: Mark Dolan, Santa Rosa, CA (US); Stuart Kari, Windsor, CA (US); Christopher W. Storment, Sonoma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/209,081

(22) Filed: Mar. 13, 2014

(65) Prior Publication Data

US 2014/0277382 A1    Sep. 18, 2014

Related U.S. Application Data

(60) Provisional application No. 61/781,717, filed on Mar. 14, 2013.

(51) Int. Cl.

| | | |
|---|---|---|
| *A61F 2/90* | (2013.01) | |
| *B23K 26/38* | (2014.01) | |
| *B22C 9/24* | (2006.01) | |
| *B22C 9/00* | (2006.01) | |

(Continued)

(52) U.S. Cl.
CPC . *A61F 2/90* (2013.01); *A61F 2/91* (2013.01); *A61F 2/915* (2013.01); *B22C 9/00* (2013.01); *B23K 26/38* (2013.01); *A61F 2240/001* (2013.01); *A61F 2250/0068* (2013.01)

(58) Field of Classification Search
CPC ..... A61F 2/90; A61F 2240/00; B23K 26/38; B22C 9/24
USPC ............ 427/2.24, 2.25; 623/1.15, 1.42, 1.46
See application file for complete search history.

(56) References Cited

U.S. PATENT DOCUMENTS

| | | | |
|---|---|---|---|
| 2,153,936 | A | 4/1939 | Owens et al. |
| 4,531,933 | A | 7/1985 | Norton et al. |

(Continued)

FOREIGN PATENT DOCUMENTS

| | | |
|---|---|---|
| EP | 836839 A2 | 10/1997 |
| EP | 1600534 | 11/2005 |

(Continued)

OTHER PUBLICATIONS

U.S. Appl. No. 09/716,146, filed Nov. 17, 2000, Boyle.

(Continued)

*Primary Examiner* — Cachet Sellman (57) ABSTRACT

A method for manufacturing a stent includes forming a stent blank from a first material, the stent blank comprising a plurality of struts and a plurality of crowns, each crown connecting at least two struts, and a plurality of slots in at least some of the plurality of struts and/or the plurality of crowns, depositing a second material over outer surfaces of the struts and the crowns and in the slots to encase the stent blank in the second material, creating at least one opening through the second material, and removing the first material to form a stent comprising the second material, the stent having a continuous lumen from one end of the stent to the other end of the stent, the continuous lumen being partitioned in portions corresponding to the locations of the slots in the stent blank. The lumen may then be filled with a therapeutic substance.

21 Claims, 4 Drawing Sheets

(51) Int. Cl.
*A61F 2/91* (2013.01)
*A61F 2/915* (2013.01)

(56) References Cited

U.S. PATENT DOCUMENTS

| | | | |
|---|---|---|---|
| 4,643,716 A | 2/1987 | Drach | |
| 4,720,384 A | 1/1988 | DiLuccio et al. | |
| 4,763,647 A | 8/1988 | Gambale | |
| 4,800,082 A | 1/1989 | Karbowski et al. | |
| 4,813,925 A | 3/1989 | Anderson, Jr. et al. | |
| 4,886,062 A | 12/1989 | Wiktor | |
| 4,913,683 A | 4/1990 | Gregory | |
| 5,019,090 A | 5/1991 | Pinchuk | |
| 5,063,935 A | 11/1991 | Gambale | |
| 5,133,732 A | 7/1992 | Wiktor | |
| 5,154,705 A | 10/1992 | Fleischhacker et al. | |
| 5,234,456 A | 8/1993 | Silvestrini | |
| 5,306,250 A | 4/1994 | March et al. | |
| 5,345,945 A | 9/1994 | Hodgson et al. | |
| 5,536,274 A | 7/1996 | Neuss | |
| 5,538,735 A | 7/1996 | Ahn | |
| 5,569,197 A | 10/1996 | Helmus et al. | |
| 5,605,162 A | 2/1997 | Mirzaee et al. | |
| 5,630,840 A | 5/1997 | Mayer | |
| 5,670,161 A | 9/1997 | Healy et al. | |
| 5,772,864 A * | 6/1998 | Møller et al. | 205/73 |
| 5,782,903 A | 7/1998 | Wiktor | |
| 5,795,318 A | 8/1998 | Wang et al. | |
| 5,824,045 A | 10/1998 | Alt | |
| 5,843,117 A | 12/1998 | Alt et al. | |
| 5,882,335 A | 3/1999 | Leone et al. | |
| 5,891,108 A | 4/1999 | Leone et al. | |
| 5,902,266 A | 5/1999 | Leone et al. | |
| 5,957,903 A | 9/1999 | Mirzaee et al. | |
| 6,022,369 A | 2/2000 | Jacobsen et al. | |
| 6,063,101 A | 5/2000 | Jacobsen et al. | |
| 6,071,305 A | 6/2000 | Brown et al. | |
| 6,099,561 A | 8/2000 | Alt | |
| 6,136,023 A | 10/2000 | Boyle | |
| 6,248,190 B1 | 6/2001 | Stinson | |
| 6,358,276 B1 | 3/2002 | Edwin | |
| 6,478,778 B1 | 11/2002 | Jacobsen et al. | |
| 6,497,709 B1 | 12/2002 | Heath | |
| 6,558,422 B1 | 5/2003 | Baker et al. | |
| 6,623,519 B2 | 9/2003 | Edwin et al. | |
| 6,641,607 B1 | 11/2003 | Hossainy et al. | |
| 6,656,162 B2 | 12/2003 | Santini, Jr. et al. | |
| 6,699,281 B2 | 3/2004 | Vallana et al. | |
| 6,752,829 B2 | 6/2004 | Kocur et al. | |
| 6,783,543 B2 | 8/2004 | Jang | |
| 6,938,668 B2 * | 9/2005 | Whicher et al. | 164/46 |
| 6,989,071 B2 | 1/2006 | Kocur et al. | |
| 7,037,330 B1 | 5/2006 | Rivelli et al. | |
| 7,041,130 B2 | 5/2006 | Santini, Jr. et al. | |
| 7,044,965 B1 | 5/2006 | Spielberg | |
| 7,060,093 B2 | 6/2006 | Dang et al. | |
| 7,101,392 B2 | 9/2006 | Heath | |
| 7,122,048 B2 | 10/2006 | Dimatteo et al. | |
| 7,135,039 B2 | 11/2006 | De Scheerder et al. | |
| 7,182,735 B2 | 2/2007 | Shireman et al. | |
| 7,288,084 B2 | 10/2007 | Li | |
| 7,316,565 B2 | 1/2008 | Liao | |
| 7,344,563 B2 | 3/2008 | Vallana et al. | |
| 7,384,660 B2 | 6/2008 | Hossainy et al. | |
| 7,400,931 B2 | 7/2008 | Mandrusov et al. | |
| 7,419,681 B2 | 9/2008 | Tormala et al. | |
| 7,455,667 B2 | 11/2008 | Uhland et al. | |
| 7,575,593 B2 | 8/2009 | Rea et al. | |
| 7,736,687 B2 * | 6/2010 | Sims et al. | 427/2.1 |
| 2002/0038145 A1 * | 3/2002 | Jang | 623/1.15 |
| 2002/0065548 A1 | 5/2002 | Birdsall et al. | |
| 2002/0087209 A1 | 7/2002 | Edwin et al. | |
| 2002/0103527 A1 | 8/2002 | Kocur et al. | |
| 2002/0138048 A1 | 9/2002 | Tuch | |
| 2003/0021825 A1 | 1/2003 | Pathak et al. | |
| 2003/0068353 A1 | 4/2003 | Chen et al. | |
| 2003/0125803 A1 | 7/2003 | Vallana et al. | |
| 2003/0208256 A1 | 11/2003 | DiMatteo et al. | |
| 2004/0006382 A1 | 1/2004 | Sohier | |
| 2004/0024449 A1 | 2/2004 | Boyle | |
| 2004/0037889 A1 | 2/2004 | Richeal et al. | |
| 2004/0106984 A1 | 6/2004 | Stinson | |
| 2004/0133270 A1 | 7/2004 | Grandt | |
| 2004/0148012 A9 | 7/2004 | Jang | |
| 2005/0043783 A1 | 2/2005 | Amis et al. | |
| 2005/0060020 A1 | 3/2005 | Jenson | |
| 2005/0070996 A1 | 3/2005 | Dinh et al. | |
| 2005/0080481 A1 | 4/2005 | Madda et al. | |
| 2005/0131521 A1 * | 6/2005 | Marton | 623/1.13 |
| 2005/0145307 A1 | 7/2005 | Shireman et al. | |
| 2005/0177226 A1 | 8/2005 | Banik et al. | |
| 2005/0186241 A1 | 8/2005 | Boyle et al. | |
| 2005/0208100 A1 | 9/2005 | Weber et al. | |
| 2005/0272806 A1 | 12/2005 | Falotico et al. | |
| 2005/0278016 A1 * | 12/2005 | Welsh et al. | 623/1.42 |
| 2006/0004437 A1 | 1/2006 | Jayaraman | |
| 2006/0064157 A1 | 3/2006 | Shanley | |
| 2006/0122689 A1 | 6/2006 | Kocur et al. | |
| 2006/0129231 A1 | 6/2006 | De Scheerder et al. | |
| 2006/0147489 A1 | 7/2006 | Shanley et al. | |
| 2006/0155369 A1 | 7/2006 | Edwin et al. | |
| 2006/0212109 A1 | 9/2006 | Sirhan et al. | |
| 2006/0224234 A1 | 10/2006 | Jayaraman | |
| 2006/0224237 A1 | 10/2006 | Furst et al. | |
| 2007/0005124 A1 | 1/2007 | De Scheerder et al. | |
| 2007/0027531 A1 | 2/2007 | Dimatteo et al. | |
| 2007/0043423 A1 | 2/2007 | Grewe | |
| 2007/0055352 A1 | 3/2007 | Naimark et al. | |
| 2007/0061007 A1 | 3/2007 | Nolting | |
| 2007/0112417 A1 | 5/2007 | Shanley et al. | |
| 2007/0123805 A1 | 5/2007 | Shireman et al. | |
| 2007/0168021 A1 | 7/2007 | Holmes, Jr. et al. | |
| 2007/0173923 A1 | 7/2007 | Savage et al. | |
| 2007/0219628 A1 | 9/2007 | Shanley et al. | |
| 2007/0282419 A1 | 12/2007 | Hilaire et al. | |
| 2008/0003251 A1 | 1/2008 | Zhou | |
| 2008/0051882 A1 | 2/2008 | Rubin | |
| 2008/0065201 A1 | 3/2008 | Li | |
| 2008/0077233 A1 | 3/2008 | Diaz et al. | |
| 2008/0183281 A1 | 7/2008 | Rea et al. | |
| 2008/0188925 A1 | 8/2008 | Zhao | |
| 2008/0195170 A1 | 8/2008 | Asgari | |
| 2008/0195196 A1 | 8/2008 | Asgari | |
| 2008/0234809 A1 | 9/2008 | Greenan | |
| 2008/0249599 A1 | 10/2008 | Allen et al. | |
| 2008/0255659 A1 | 10/2008 | Huang et al. | |
| 2008/0276935 A1 | 11/2008 | Wang | |
| 2008/0306579 A1 | 12/2008 | Dolan et al. | |
| 2009/0024209 A1 | 1/2009 | Ozdil et al. | |
| 2009/0024210 A1 | 1/2009 | Klocke et al. | |
| 2009/0035351 A1 | 2/2009 | Berglund et al. | |
| 2009/0061071 A1 | 3/2009 | McMorrow et al. | |
| 2009/0093871 A1 | 4/2009 | Rea et al. | |
| 2009/0132031 A1 | 5/2009 | Cook et al. | |
| 2009/0143855 A1 | 6/2009 | Weber et al. | |
| 2009/0157172 A1 | 6/2009 | Kokate et al. | |
| 2009/0163995 A1 | 6/2009 | Shanley et al. | |
| 2009/0192593 A1 | 7/2009 | Meyer et al. | |
| 2009/0220612 A1 | 9/2009 | Perera | |
| 2009/0228095 A1 | 9/2009 | Shanley et al. | |
| 2009/0281615 A1 | 11/2009 | Kocur et al. | |
| 2009/0312833 A1 | 12/2009 | Tittelbach et al. | |
| 2009/0319026 A1 | 12/2009 | Meyer | |
| 2010/0010621 A1 | 1/2010 | Klocke | |
| 2010/0023115 A1 | 1/2010 | Robaina et al. | |
| 2010/0036482 A1 | 2/2010 | Svrluga et al. | |
| 2010/0057196 A1 | 3/2010 | Pathak | |
| 2010/0070022 A1 | 3/2010 | Kuehling | |
| 2010/0082096 A1 | 4/2010 | Gregorich | |
| 2010/0145437 A1 | 6/2010 | Girton et al. | |
| 2011/0008405 A1 | 1/2011 | Birdsall et al. | |
| 2011/0264187 A1 | 10/2011 | Melder | |
| 2012/0009325 A1 * | 1/2012 | Storment | 427/2.25 |
| 2012/0067008 A1 | 3/2012 | Bienvenu | |

(56) References Cited

U.S. PATENT DOCUMENTS

| | | |
|---|---|---|
| 2012/0070562 A1 | 3/2012 | Avelar et al. |
| 2012/0216916 A1* | 8/2012 | Pacetti .................... A61F 2/915 141/98 |
| 2013/0284310 A1 | 10/2013 | Peterson |
| 2013/0284311 A1 | 10/2013 | Peterson |

FOREIGN PATENT DOCUMENTS

| | | |
|---|---|---|
| EP | 836839 B1 | 7/2006 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO01/55473 | 8/2001 |
| WO | WO02/060506 | 8/2002 |
| WO | WO03/092547 | 11/2003 |
| WO | WO2004/091686 | 10/2004 |
| WO | WO2007/021749 | 2/2007 |
| WO | WO2007/033282 | 3/2007 |
| WO | WO2011/008896 | 1/2011 |
| WO | WO2012/036929 | 3/2012 |

OTHER PUBLICATIONS

U.S. Appl. No. 12/428,581, filed Apr. 23, 2009, Hoff et al.
U.S. Appl. No. 12/500,359, filed Jul. 9, 2009, Storment et al.
U.S. Appl. No. 61/244,049, filed Sep. 20, 2009, Thompson et al.
U.S. Appl. No. 61/244,050, filed Sep. 20, 2009, Silver et al.
Basarir et al., "Osseointegration in Arthroplasty: Can Simvastatin Promote Bone Response to Implants?" International Orthopaedics (SICOT)(2009) 33:855-859.
Polacco et al. "Biodegradable Hollow Fibres Containing Drug-Loaded Nanoparticles as Controlled Release Systems" Polym International 51:1464-1472 (2002).
Derle et al., "Particle Engineering Techniques to Enhance Dissolution of Poorly Water Soluble Drugs" International Journal of Current Pharmaceutical Research, vol. 2, Issue 1, 2010, pp. 10-15.
Purvis et al., "Cryogenic Liquids, Nanoparticles, and Microencapsulation" International Journal of Pharmaceutics, 2006.
"Breakthrough Solubilization Technology Targets Stubborn Drug Candidates" Dowpharma.
"Supercritical Carbon-Dioxide Cleaning Defined" Supercritical Carbon-Dioxide Cleaning Technology Review, Jul. 1996.
Berger "Coating Drug-Eluting Arterial Stents Using Ultrasonic Spray Nozzle" ILASS Americas, 19$^{th}$ Annual Conference on Liquid Atomization and Spray Systems, May 2006.
Kim et al. "Electrically Controlled Hydrophobicity in a Surface Modified Nanoporous Carbon" Applied Physics Letters 98, 053106 (2011).
Vallet et al. "Electrowetting of Water and Aqueous Solutions on Poly(ethylene Terephthalate) Insulating Films" Polymer vol. 37, No. 12, pp. 2465-2470, 1996.
PCT Search Report PCT/US2014/026648.
PCT Search Report PCT/US2010/039087.
PCT Search Report PCT/US2010/049439.
PCT Search Report PCT/US2010/049437.
PCT Search Report PCT/US2010/049434.

\* cited by examiner

METHOD FOR MANUFACTURING A STENT AND STENT MANUFACTURED THEREBY

CROSS-REFERENCE TO RELATED APPLICATIONS

This application claims the benefit of priority from U.S. Provisional Patent Application No. 61/781,717, filed Mar. 14, 2013, which is incorporated herein by reference in its entirety.

FIELD

The present invention is related to a method for manufacturing a stent and a stent manufactured thereby.

BACKGROUND

Drug-eluting implantable medical devices have become popular in recent times for their ability to perform their primary function (such as structural support of a vessel, for example) and their ability to medically treat the area in which they are implanted.

For example, drug-eluting stents have been used to act as scaffolds to support lumens of vessels in open positions and to prevent restenosis in coronary arteries. Drug-eluting stents may administer therapeutic agents such as anti-inflammatory compounds that block local invasion/activation of monocytes, thus preventing the secretion of growth factors that may trigger vascular smooth muscle cell proliferation and migration. Other potentially anti-restenotic compounds, including antiproliferative agents, may also be administered. Other classes of drugs such as anti-thrombotics, anti-oxidants, platelet aggregation inhibitors and cytostatic agents have also been suggested for anti-restenotic use.

Drug-eluting stents may be coated with a polymeric material which, in turn, is impregnated with a drug or a combination of drugs. Once the stent is implanted at a target location, the drug is released from the polymer for treatment of the local tissues. The drug is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Stents can be manufactured from a variety of materials. These materials include, but are not limited to, metals and polymers. Both metal and polymer vascular stents have been associated with thrombosis, chronic inflammation at the implantation site, and impaired remodeling at the stent site. It has been proposed that limiting the exposure of the vessel to the stent to the immediate intervention period would reduce late thrombosis chronic inflammation and allow the vessel to return to its normal functional state. One means to produce a temporary stent is to implant a bioabsorbable or biodegradable stent.

There are several parameters to consider in the selection of a bioabsorbable material for stent manufacture. These include, but are not limited to, the strength of the material to avoid potential immediate recoil of the vessel, the rate of degradation and corrosion, and biocompatibility with the vessel wall. Additionally, it may be desirable to include therapeutic agents in the bioabsorbable stent such that the therapeutic agent is released at the implantation site during degradation of the stent. The mechanical properties of the stent and release profiles of therapeutic agents directly depend on the rate of degradation of the stent material which is controlled by selection of the stent materials, passivation agents and the manufacturing process of the stent. Currently there are two types of materials, i.e. polymers and metals, used in bioabsorbable stents.

Bioabsorbable polymer stent materials have several significant limitations. Their radial strength is lower than metallic materials, which can result in early recoil post implantation and other mechanical tradeoffs. Also, bioabsorbable polymer stent materials are associated with a significant degree of local inflammation, and they have a relatively slow bioabsorption rate. Additionally, polymeric stents are often radiolucent which impairs accurate positioning within a vessel lumen. The physical limitations of the polymer require thick struts to increase radial strength which impedes their profile and delivery capabilities. Non-biodegradable markers are also needed to provide radiopacity. Metal bioabsorbable stents are attractive since they have the potential to perform similarly to durable metal stents.

There exists a need for a bioabsorbable, drug-eluting stent that incorporates the strength characteristics of a metal with nonpolymer drug eluting properties.

SUMMARY

According to an aspect of the invention, there is provided a method for manufacturing a stent. The method includes forming a stent blank from a first material. The stent blank includes a plurality of struts and a plurality of crowns, each crown connecting at least two struts, and a plurality of slots in at least some of the plurality of struts and/or the plurality of crowns. The method includes depositing a second material over outer surfaces of the struts and the crowns and in the slots to encase the stent blank in the second material, creating an opening through the second material, and removing the first material to form a stent comprising the second material, the stent having a continuous lumen from one end of the stent to the other end of the stent, the continuous lumen being partitioned in portions corresponding to the locations of the slots in the stent blank.

In an embodiment, forming the stent blank includes laser cutting a cylindrical substrate that includes the first material to create a pattern comprising the struts and the crowns. In an embodiment, forming the stent blank includes etching a cylindrical substrate that includes the first material to create a pattern comprising the struts and the crowns.

In an embodiment, forming the stent blank further includes laser cutting the plurality of slots. In an embodiment, forming the stent blank further includes etching the plurality of slots.

In an embodiment, the method further includes cleaning the stent blank prior to depositing the second material.

In an embodiment, the depositing includes electron deposition of the second material onto the outer surfaces of the struts and the crowns and in the slots. In an embodiment, the depositing includes electrochemical deposition of the second material onto the outer surfaces of the struts and the crowns and in the slots. In an embodiment, the depositing includes sputter coating the second material onto the outer surfaces of the struts and the crowns and in the slots.

In an embodiment, the depositing includes depositing the second material over the outer surfaces of the struts and the crowns and in the slots to create a coating having a thickness of 10-30 µm. In an embodiment, the depositing includes depositing the second material over the outer surfaces of the struts and the crowns to create a coating having a thickness of at least one-half the width of the slots.

In an embodiment, the first material includes tantalum. In an embodiment, the second material includes iron.

In an embodiment, the method includes depositing a third material over at least the outer surfaces of the struts and the crowns, the third material being radiopaque. In an embodiment, the third material comprises platinum.

In an embodiment, the method includes filling the lumen with a therapeutic substance.

According to an aspect of the invention, a stent is manufactured by a method that includes forming a stent blank from a first material. The stent blank includes a plurality of struts and a plurality of crowns, each crown connecting at least two struts, and a plurality of slots in at least some of the plurality of struts and/or the plurality of crowns. The method includes depositing a second material over outer surfaces of the struts and the crowns and in the slots to encase the stent blank in the second material, creating an opening through the second material; and removing the first material to form a stent comprising the second material and having a continuous lumen from one end of the stent to the other end of the stent.

According to an aspect of the invention, a stent is manufactured by a method that includes forming a stent blank from a first material. The stent blank includes a plurality of struts and a plurality of crowns, each crown connecting at least two struts, and a plurality of slots in at least some of the plurality of struts and/or the plurality of crowns. The method includes depositing a second material over outer surfaces of the struts and the crowns and in the slots to encase the stent blank in the second material, creating an opening through the second material, removing the first material to form a stent comprising the second material and having a continuous lumen from one end of the stent to the other end of the stent, and filling the lumen with a therapeutic substance.

BRIEF DESCRIPTION OF DRAWINGS

The foregoing and other features and advantages of the invention be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, where like reference numbers indicate identical or functionally similar elements.

Figure 1:
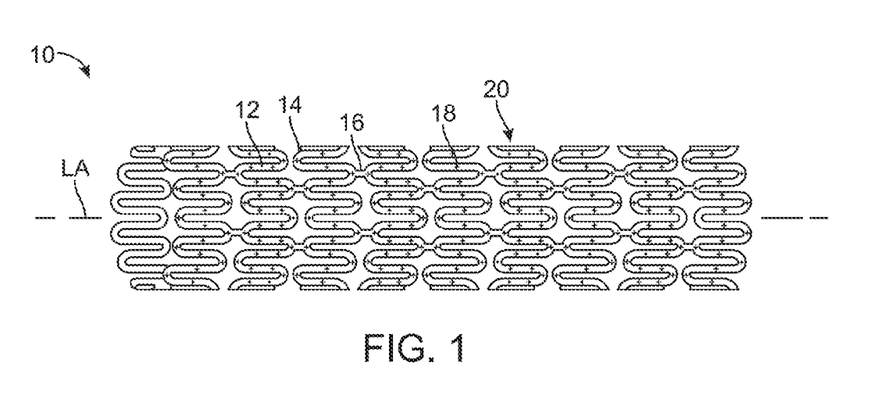
FIG. 1 illustrates a stent in accordance with an embodiment of the invention that has been made by a manufacturing method according to an embodiment of the invention.

FIG. 1 illustrates a stent 10 that has been manufactured in accordance with embodiments of the present invention. As illustrated in FIG. 1, the stent 10 includes a plurality of struts 12 or substantially straight portions, and a plurality of crowns 14 or bends. Each crown 14 connects at least two struts 12. The stent 10 includes a plurality of bands 20 or rings, each of which is comprised of a plurality of struts 12 and a plurality of crowns 14 that are connected to form a continuous band 20 centered on a longitudinal axis LA of the stent 10. Each band 20 may be connected to an adjacent band 20 with a connector 16 that extends from a crown 14 of one band 20 to a crown 14 of an adjacent band 20. In an embodiment, the connectors 16 may be used to connect struts 12 of adjacent bands 20. The connectors 16 may be substantially straight, like a strut, or may be curved.

As discussed in further detail below, the stent 10 includes a substance, such as a therapeutic substance or agent, disposed within a pair of parallel lumens, and a plurality of openings 18 in at least some of the plurality of struts 12 and/or plurality of crowns 14. More or less openings 18 may be provided. In an embodiment, the openings 18 may also be provided in at least some of the connectors 16. The illustrated embodiment is not intended to be limiting in any way.

Figure 2:
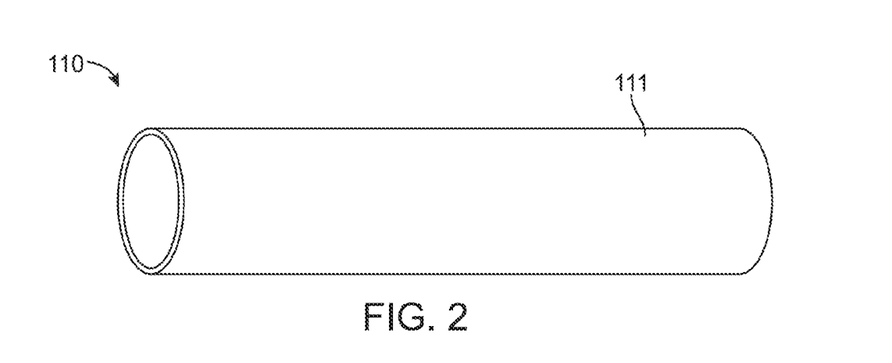
FIG. 2 illustrates a cylindrical substrate comprising a first material from which a stent blank is formed, in according with an embodiment of the invention.
Figure 3:
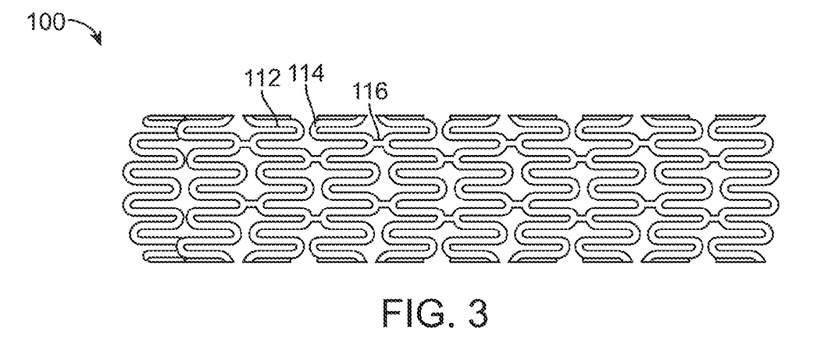
FIG. 3 illustrates a stent blank that has been formed from the cylindrical substrate of FIG. 2, in accordance with an embodiment of the invention.
Figure 4:
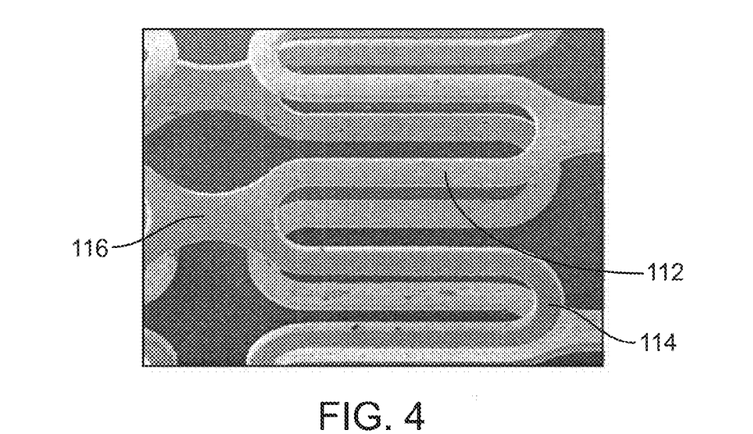
FIG. 4 is a micrograph of a portion of the stent blank of FIG. 3.

Methods for manufacturing the stent 10 according to embodiments of the present inventions will now be described. In an embodiment, a stent blank 100, such as the stent blank 100 illustrated in FIG. 3, may be formed from a cylindrical substrate 110, illustrated in FIG. 2, made from a first material 111. The cylindrical substrate 110 may be a tube or a thin plate of the first material and rolled into a tube. The first material 111 may be, for example, tantalum, tungsten, molybdenum, carbon, aluminum, silver, or copper. The cylindrical substrate 110 may be laser cut to create the desired pattern of struts 112, crowns 114, and connectors 116 to form the stent blank 100. FIG. 4 is a microphotograph illustrating the struts 112, crowns 114, and connectors 116 after the desired pattern of struts, crowns, and connectors have been formed.

In another embodiment, a cylindrical wire may be shaped into a sinusoidal waveform and wrapped around a cylindrical mandrel to form the stent blank. The wire may then be flattened against the mandrel by techniques, such as swaging. In an embodiment, the wire may have a different cross-section, such as rectangular or square. Connectors between selected crowns from adjacent wraps may be created by fusion or welding techniques.

Figure 5:
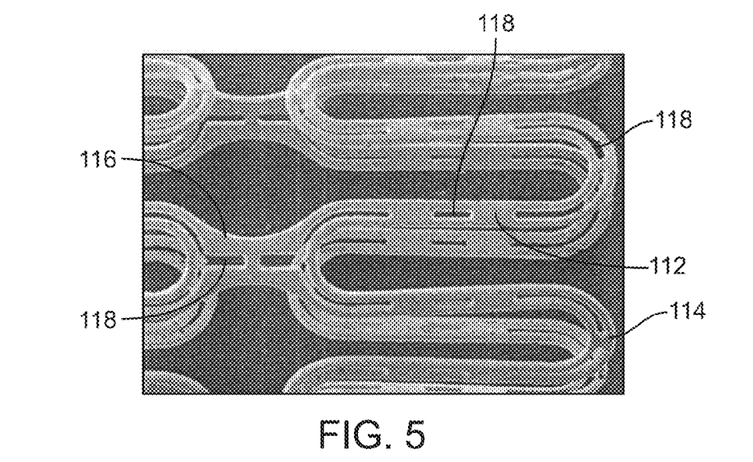
FIG. 5 is a micrograph of the portion of the stent blank with slots, in accordance with an embodiment of the invention.

As part of the same process, or subsequent to the process of forming the desired pattern of struts, crowns, and connectors. A plurality of slots 118 may also be formed in at least some of the struts 112 and/or crowns 114 and/or connectors 116, as illustrated in FIG. 5. For example, in an embodiment, the same laser may be used to cut the slots 118 into the struts 112, crowns 114, and connectors 116 at the same time the struts 112, crowns 114, and connectors 116 are cut. In an embodiment, the slots 118 may be formed at a time after the original stent blank pattern is formed. If the slots 118 are formed at a later time, the slots 118 may be cut by the same or a different laser, or the slots 118 may be etched or micro-etched from the desired struts 112, crowns 114, and/or connectors 116.

In another embodiment, the desired pattern of struts 112, crowns 114, and connectors 116, may be created from the cylindrical substrate 110 by etching. At the same time, the slots 118 may also be created by etching or micro-etching the cylindrical substrate 110. In an embodiment, the slots 118 may be formed at a later time and be etched or micro-etched, or may be cut out of the desired struts 112, crowns 114, and/or connectors 116 by a laser.

In another embodiment, the stent blank 100 and its desired pattern of struts 112, crowns 114, connectors 116, and slots 118 may be formed by three-dimensional ("3-D") printing techniques.

Figure 6:
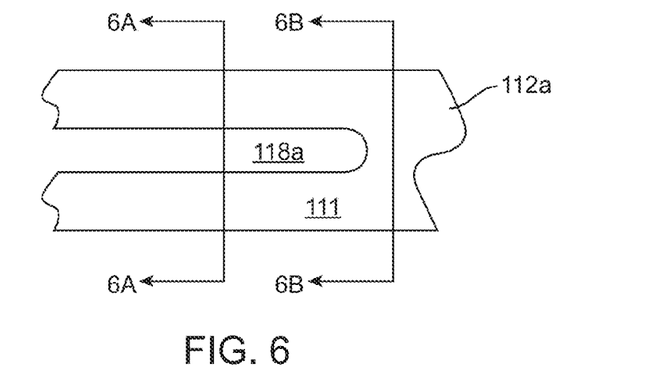
FIG. 6 illustrates a portion of the stent blank of FIG. 5.
Figure 6A:
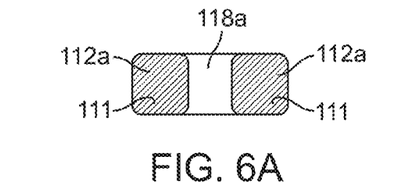
FIG. 6A illustrates a cross-section of the portion of the stent blank illustrated in FIG. 6, taken along line 6A-6A.
Figure 6B:
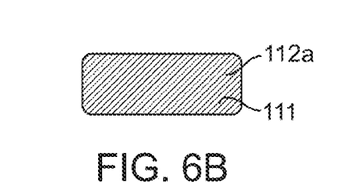
FIG. 6B illustrates a cross-section of the portion of the stent blank illustrated in FIG. 6, taken along line 6B-6B.

After the stent blank 100 having the desired pattern of struts 112, crowns 114, connectors 116, and slots 118 has been formed, as illustrated in FIG. 5, the stent blank 100 may be cleaned with an acid, or by electropolishing, or by mechanical means to remove any sharp edges, burrs and/or surface defects and provide a smooth surface. FIG. 6 illustrates a portion of the stent blank 100 after the slots 118 have been formed and the stent blank 100 has been cleaned. In the embodiment illustrated in FIG. 6, a strut 112a includes a slot 118a in a center portion thereof such that a longitudinal axis of the strut 112a and the longitudinal axis of the slot 118a are substantially aligned. A cross-section of the strut 112a along line 6A-6A is illustrated in FIG. 6A, and a cross-section of the strut 112a along line 6B-6B is illustrated in FIG. 6B.

After the stent blank 100 has been cleaned, a second material 121 may then be deposited over the outer surfaces of the stent blank 100 and into the slots 118 so as to encase, i.e. completely surround and envelope, the stent blank 100. The second material 121 may be a material known to be bioabsorbable, such as iron, magnesium, zinc, alloys of iron, alloys of magnesium, and alloys of zinc. In an embodiment, a third material may be mixed or alloyed with the second material 121 or may be deposited onto at least some of the outer surfaces of the stent blank 100 or in the slots 118 prior to the deposition of the second material 121. For example, in an embodiment, the third material may be radiopaque and may comprise, for example, platinum.

Various methods may be used to deposit the second material 121 over the first material 111 of the stent blank 100. For example, in an embodiment, electron deposition may be used to deposit the second material 121 over the outer surfaces and into the slots 118 of the stent blank 100. In an embodiment, the second material 121 may be sputter coated over the outer surfaces and into the slots 118 of the stent blank 100. Other coating techniques, such as electrodeposition, chemical vapor deposition (CVD), or plasma-enhanced chemical vapor deposition (PECVD) may be used to coat the second material 121 onto surfaces of the first material 111. In an embodiment, the second material 121 may be deposited so that it forms a coating having a thickness of 10-30 µm over the stent blank 100. In an embodiment, the thickness may be about 25 µm. In an embodiment, the second material 121 may be deposited over the outer surfaces of the stent blank 100 to create a coating having a thickness of at least one-half the width of the slots 118. In an embodiment, the second material 121 may be deposited over the outer surfaces of the stent blank 100 to create a coating having a thickness of equal to or less than one-half the width of the slots 118.

Figure 7:
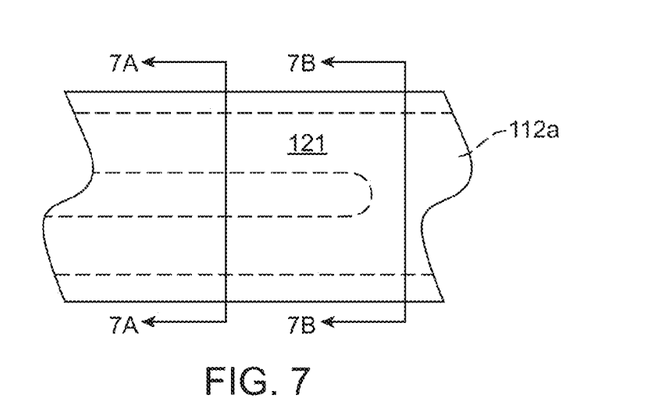
FIG. 7 illustrates a cross-section of the portion of the stent blank illustrated in FIG. 6, after a second material has been deposited on the outer surfaces of the stent blank and in the slots of the stent blank, in accordance with an embodiment of the invention.
Figure 7A:
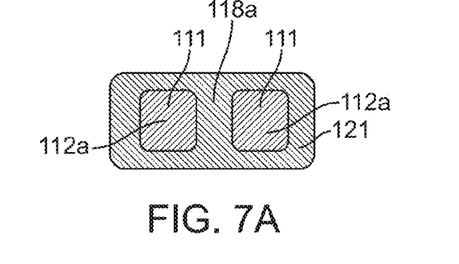
FIG. 7A illustrates a cross-section of the portion of the coated stent blank illustrated in FIG. 7, taken along line 7A-7A.
Figure 7B:
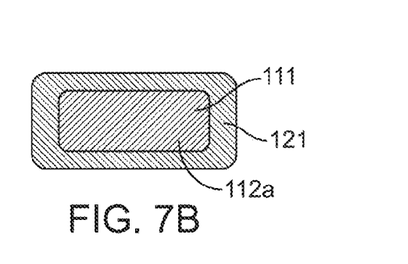
FIG. 7B illustrates a cross-section of the portion of the coated stent blank illustrated in FIG. 7, taken along line 7B-7B.

FIG. 7 illustrates the same portion of the strut 112a illustrated in FIG. 6 after the stent blank has been encased in the second material 121. A cross-section of the strut 112a and the second material 121 along line 7A-7A is illustrated in FIG. 7A, and a cross-section of the strut 112a and the second material 121 along line 7B-7B is illustrated in FIG. 7B.

Figure 8A:
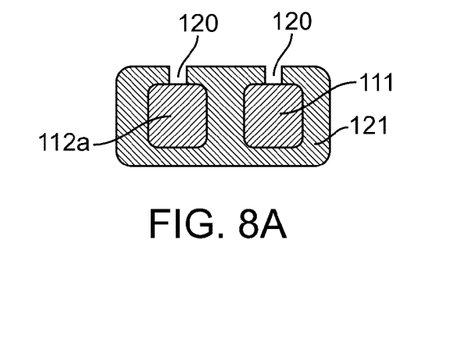
FIG. 8A illustrates the cross-section of the portion of the coated stent blank illustrated in FIG. 7A after openings through the second material have been created, in accordance with an embodiment of the invention.
Figure 8B:
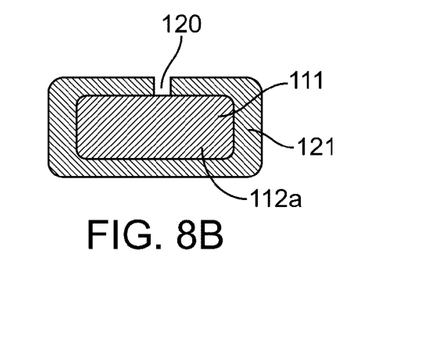
FIG. 8B illustrates the cross-section of the portion of the coated stent blank illustrated in FIG. 7B after an opening through the second material has been created, in accordance with an embodiment of the invention.

Openings 120 may be created through the second material 121 so as to expose the first material 111, as illustrated in FIGS. 8A and 8B. The first material 111 may then be removed, for example, by chemical etching, or other methods. The removal of the first material 111, which is a sacrificial material, is accomplished without damaging the struts 12, crowns 14, or connectors 16. For example, and not by way of limitation, if the first material 111 is copper or silver, it may be removed using nitric acid. Phosphoric acid mixtures may be used to remove aluminum. Gas or plasma etching may be used to remove tungsten, molybdenum, tantalum or carbon.

Various materials may be used for the first material 111, and various materials may be used for the second material 121. The materials and etchants are selected such that the etchants dissolve or otherwise remove the first material 111 without damaging the second material 121. U.S. patent application Ser. No. 12/500,359, filed Jul. 9, 2009, and published as U.S. 2011/0008405 on Jan. 13, 2011, incorporated herein in its entirety by reference, discloses various etchants that remove one metal or alloy without damaging another metal or alloy.

Figure 9A:
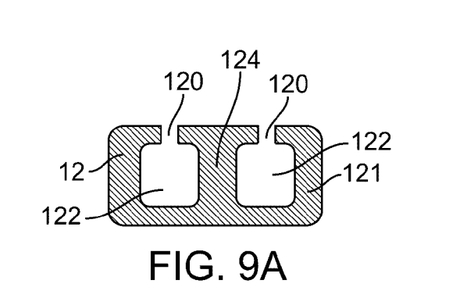
FIG. 9A illustrates the cross-section of the portion of the coated stent blank illustrated in FIG. 8A after the first material of the stent blank has been removed through the openings, in accordance with an embodiment of the invention.
Figure 9B:
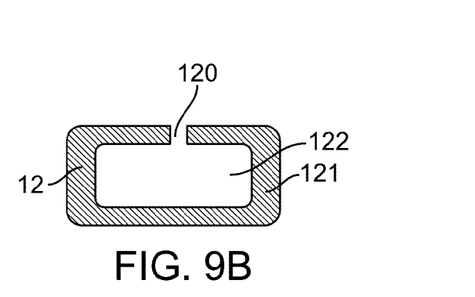
FIG. 9B illustrates the cross-section of the portion of the coated stent blank illustrated in FIG. 8B after the first material of the stent blank has been removed through the opening, in accordance with an embodiment of the invention.

Upon removal of the first material 111, the second material 121 remains as the struts 12, crowns 14, and connectors 16 of the stent 10, and the stent 10 has a continuous lumen 122 from one end of the stent 10 to the other end of the stent 10, as illustrated, for example, in FIGS. 9A and 9B. For the portions of the stent 10 that corresponded to the portions of the stent blank 100 that included slots 118, the lumen 122 remains continuous, but is partitioned with a strengthening member 124 comprised of the second material 121 that was previously deposited into the slots 118 in the center of the lumen 122, as illustrated in FIG. 9A. For example, for the portion of the strut 12 that corresponds to the portion of the strut 112a of the stent blank illustrated in FIG. 6, the strengthening member 124 is oriented parallel with the strut 12 and does not create any discontinuity within the lumen 122 so that the lumen remains continuous from one end of the stent 10 to the other end of the stent 10.

Figure 10A:
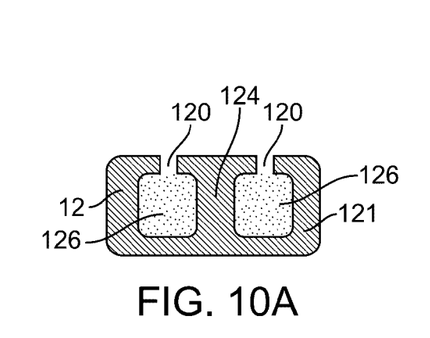
FIG. 10A illustrates the cross-section of the portion of the stent corresponding to FIG. 9A after a therapeutic agent has been introduced into a partitioned lumen that was created upon removal of the first material, in accordance with an embodiment of the invention.
Figure 10B:
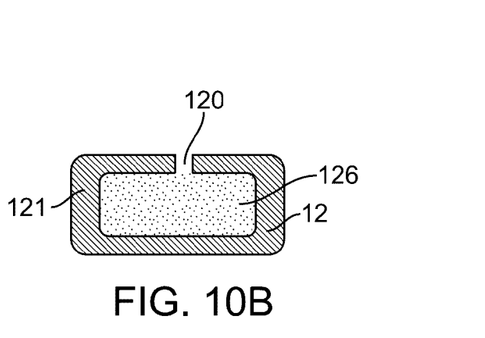
FIG. 10B illustrates the cross-section of the portion of the stent corresponding to FIG. 9B after the therapeutic agent has been introduced into the lumen that was created upon removal of the first material, in accordance with an embodiment of the invention.

If the stent 10 is a drug-eluting stent, the continuous lumen 122 may then be filled with an adjunctive or therapeutic substance 126, as illustrated in FIGS. 10A and 10B. The lumen 122 may be filled through the openings 120 and/or other openings created for the purpose of filling the lumen 122. Such additional openings, if used, may then be closed after the lumen 122 is filled with the adjunctive or therapeutic substance 126. The lumen 122 is filled with the adjunctive or therapeutic substance by various methods. For example, a liquid or semi-liquid state of the adjunctive or therapeutic substance may be introduced into the lumen 122 by one or more methods described in U.S. patent application Ser. No. 13/457,398, filed Apr. 27, 2012, published as United States Patent Application Publication No. 2013/0284310 on Oct. 31, 2013 and entitled "Apparatus and Methods for Filling a Drug Eluting Medical Device Via Capillary Action", and in U.S. patent application Ser. No. 13/457,418, filed Apr. 27, 2012, published as United States Patent Application Publication No. 2013/0284311 on Oct. 31, 2013 and entitled "Apparatus and Methods for Filling a Drug Eluting Medical Device Via Capillary Action", both of which are incorporated herein by reference in their entireties. In an embodiment, the lumen 122 may be filled with a suitable visopaque or iodine/dense metal solvent to increase the radiopacity of the stent 10 while the stent 10 is being implanted in a vessel, but then vanishes with dissolution. In an embodiment, the lumen may be filled with combinations of substances that increase the radiopacity of the stent while the stent is being implanted in a vessel and also provide a therapeutic effect to the vessel after the stent is implanted in the vessel.

It would be understood by those of ordinary skill in the art that the openings 120 may be located at various locations along the struts 12 and crowns 14. The size, shape, and/or density (number per unit length or area) of the openings 120 may be varied along the stent 10. Such variations may alter the elution rate of the adjunctive or therapeutic substance along the stent 10. For example, and not by way of limitation, more or larger openings may be providing in the middle portion of the stent 10 and less or smaller openings may be provided near the ends of the stent 10.

To determine the beneficial effect of having a partitioned lumen within a strut, crown, or connector, finite element analysis (FEA) was completed for various cross-sections of a strut made from iron (Fe). Based on literature, the mechanical properties of iron were estimated to be 211 GPa for the Young's Modulus, 300 MPa for the Yield Stress, 135 MPa for the Plastic Modulus, and 0.29 for Poisson's Ratio. Four single strut models were completed using FEA software, and the characteristics of the struts and the predicted strength results, are listed in Table I:

TABLE I

Modeling Results

| | Model 1 Solid Strut | Model 2 Single Lumen | Model 3 Single Lumen | Model 4 Partitioned Lumen |
|---|---|---|---|---|
| Strut Volume (mm$^3$) | 0.02 | 0.02 | 0.025 | 0.025 |
| Mass (mg) | 0.16 | 0.11 | 0.12 | 0.16 |
| Surface Area (mm$^2$) | 0.7 | 1.09 | 1.22 | 1.44 |
| Strength (mN) | 42 | 35 | 53 | 63 |

The modeling results indicate that with a constant material and contour geometry, i.e. constant segment length and deployment angles, the strength of the strut may be increased by increasing the thickness/volume of the strut. In addition, the strength of the strut may be increased by hollowing out the strut, i.e. providing a lumen or lumens in the strut, and increasing the volume of the strut. The Model 1 strut, which is solid in cross-section, but thinner than the struts of Models 3 and 4, is predicted to have a strength of 42 mN, while the Model 3 strut, which contains a single lumen, but is thicker than the struts of Models 1 and 2, is predicted to have a strength of 53 mN. Further increasing the strength of the strut cannot be done by making the lumen larger, without lowering the surface area or increasing the volume of the strut. The Model 4 strut, which includes a partitioned lumen, has the same mass as, but greater surface area than, the Model 1 solid strut, and a greater mass and surface area than the Model 3 strut, and is predicted to have a strength of 63 mN, which is higher than the predicted strength of the other Models.

Embodiments of the present invention provide a stent having an enhanced internal three-dimensional geometry that includes a continuous lumen from one end of the stent to the other end of the stent, and portions of the stent in which the lumen is partitioned with strengthening members in the partitioned portion of the lumen. It may be desirable to locate a partitioned lumen with a strengthening member in at least 30% of a curved section, i.e. crown, and/or areas of potential or anticipated high strain, and/or transition areas between straight and curved sections, i.e. between struts and crowns, or multi-curved sections. Although the illustrated embodiment depicts a strengthening member that resembles an I-beam, other shapes may be created by controlling the shape of the stent blank, including the slots.

The enhanced three-dimensional geometry may further increase the strength of the stent, without increasing the total volume of the stent material. For bioabsorbable stents, it is desirable to optimize the ratio of the surface area to volume to minimize the overall degradation time. For example, although iron is known to have good strength and mechanical properties, iron has a relatively slow degradation rate. By forming the stent in accordance to embodiments of the present invention, an improved bioabsorbable, drug-eluting stent with good mechanical properties and short degradation times may be provided.

The stent 10 may be used conventionally in blood vessels of the body to support such a vessel after an angioplasty procedure. It is known that certain drugs eluted from stents may prevent restenosis or other complications associated with angioplasty or stents. The stent 10 may alternatively be used in other organs or tissues of the body for delivery of drugs to treat tumors, inflammation, erectile dysfunction, nervous conditions, or other conditions that would be apparent to those skilled in the art.

The therapeutic substance or drug 126 may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., TAXOTERE® from Aventis S. A., Frankfurt, Germany), methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., PRINIVIL® and PRINZIDE® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include nitric oxide, alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to phosphorus ($P^{32}$), palladium ($Pd^{103}$), cesium ($Cs^{131}$), Iridium ($Ir^{192}$) and iodine ($I^{125}$). The substances or agents are provided by way of example and are not meant to be limiting. Other therapeutic substances are equally applicable for use with the disclosed methods and compositions.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method for manufacturing a stent, the method comprising:
    forming a stent blank from a first material, the stent blank comprising a plurality of struts and a plurality of crowns, each crown connecting at least two struts;
    forming a plurality of slots into at least some of the plurality of struts and/or the plurality of crowns, such that the plurality of slots extend through the first material to create openings through the at least some of the plurality of struts and/or the plurality of crowns;
    depositing a second material over outer surfaces of the struts and the crowns and through the slots to encase the stent blank in the second material;
    creating an opening through the second material; and
    removing the first material to form a stent comprising a plurality of struts and crowns defined by the second material, a continuous lumen is defined by the plurality of struts and crowns of the second material, the continuous lumen being partitioned in portions corresponding to the locations of the slots in the stent blank.

2. The method according to claim 1, wherein said forming the stent blank comprises laser cutting a cylindrical substrate comprising the first material to create a pattern comprising the struts and the crowns.

3. The method according to claim 2, wherein said forming further comprises laser cutting the plurality of slots.

4. The method according to claim 2, wherein said forming further comprises etching the plurality of slots.

5. The method according to claim 1, wherein said forming the stent blank comprises etching a cylindrical substrate comprising the first material to create a pattern comprising the struts and the crowns.

6. The method according to claim 5, wherein said forming further comprises etching the plurality of slots.

7. The method according to claim 5, wherein said forming further comprises laser cutting the plurality of slots.

8. The method according to claim 1, further comprising cleaning the stent blank prior to said depositing the second material.

9. The method according to claim 1, wherein said depositing comprises electron deposition of the second material onto the outer surfaces of the struts and the crowns and in the slots.

10. The method according to claim 1, wherein said depositing comprises electrochemical deposition of the second material onto the outer surfaces of the struts and the crowns and in the slots.

11. The method according to claim 1, wherein said depositing comprises sputter coating the second material onto the outer surfaces of the struts and the crowns and in the slots.

12. The method according to claim 1, wherein said depositing comprises depositing the second material over the outer surfaces of the struts and the crowns and in the slots to create a coating having a thickness of 10-30 μm.

13. The method according to claim 1, wherein said deposition comprises depositing the second material over the outer surfaces of the struts and the crowns to create a coating having a thickness of at least one-half the width of the slots.

14. The method according to claim 1, wherein the first material comprises tantalum.

15. The method according to claim 1, wherein the second material comprises iron.

16. The method according to claim 1, further comprising depositing a third material over at least the outer surfaces of the struts and the crowns before said depositing the second material, the third material being radiopaque.

17. The method according to claim 16, wherein the third material comprises platinum.

18. The method according to claim 1, further comprising filling the lumen with a therapeutic substance.

19. The method according to claim 1, further comprising forming
the plurality of slots in a center portion of at least some of the plurality of struts, such that a longitudinal axis of a strut and a longitudinal axis of a slot are substantially aligned.

20. The method according to claim 1, further comprising forming
the plurality of slots in at least some of the plurality of crowns, such that the shape of the slots and crowns have substantially the same curvature.

21. The method according to claim 1, further comprising forming
the plurality of slots in at least some of the plurality of struts and/or plurality of crowns, such that the plurality of slots extend from one side of the struts and crowns through to another side of the struts and crowns.

* * * * *